United States Patent
Allen et al.

(10) Patent No.: US 9,174,923 B2
(45) Date of Patent: *Nov. 3, 2015

(54) ALKYL LACTYLLACTATE SOLVENT COMPOSITIONS

(75) Inventors: David R Allen, Chicago, IL (US); John C Hutchison, Chicago, IL (US); Christopher D Smith, Watkinsville, GA (US); Jacqueline M Pytel, Libertyville, IL (US)

(73) Assignee: Stepan Company, Northfield, IL (US)

( * ) Notice: Subject to any disclaimer, the term of this patent is extended or adjusted under 35 U.S.C. 154(b) by 528 days.

This patent is subject to a terminal disclaimer.

(21) Appl. No.: 12/349,329

(22) Filed: Jan. 6, 2009

(65) Prior Publication Data
US 2009/0173917 A1    Jul. 9, 2009

Related U.S. Application Data

(63) Continuation of application No. PCT/US2007/072937, filed on Jul. 6, 2007.

(60) Provisional application No. 60/819,145, filed on Jul. 6, 2006, provisional application No. 60/842,476, filed on Sep. 6, 2006, provisional application No. 60/896,205, filed on Mar. 21, 2007.

(51) Int. Cl.
*C11D 17/00*    (2006.01)
*C07C 69/68*    (2006.01)
*C07C 67/31*    (2006.01)
(Continued)

(52) U.S. Cl.
CPC .............. *C07C 69/68* (2013.01); *A61K 31/22* (2013.01); *B01F 17/0021* (2013.01); *C07C 67/31* (2013.01); *B01F 1/00* (2013.01)

(58) Field of Classification Search
CPC ......... C07C 69/68; C07C 67/31; C11D 17/00
USPC ........ 514/772.2; 530/317; 528/354; 510/372, 510/340, 405, 434; 252/364; 562/589
See application file for complete search history.

(56) References Cited

U.S. PATENT DOCUMENTS 2,350,388 A    6/1944    Claborn
2,371,281 A *  3/1945    Claborn ...................... 560/185

(Continued)

FOREIGN PATENT DOCUMENTS

| CA | 2283517 A1 | 10/1998 | |
| KR | 1020050008936 | * 6/2006 | ............. C12P 41/00 |
| WO | WO96/02225 A1 | 2/1996 | |

OTHER PUBLICATIONS

Office Action in U.S. Appl. No. 12/349,316, dated Dec. 4, 2009.

(Continued)

*Primary Examiner* — Tri V Nguyen
(74) *Attorney, Agent, or Firm* — McAndrews, Held & Malloy, Ltd.

(57) ABSTRACT

Alkyl lactyllactate and alkoxylated alkyl lactyllactate compounds that are useful as solvents in a variety of applications are disclosed. The compounds are derived from a hydroxyl containing compound and a lactide or lactic acid source that has a specific chirality. The alkyl lactyllactate and alkoxylated alkyl lactyllactate compounds are particularly suitable for use as solvents in applications requiring cold tolerance performance without inclusion of additional volatile components.

14 Claims, 2 Drawing Sheets

(51) Int. Cl.
*A61K 31/22* (2006.01)
*B01F 17/00* (2006.01)
*B01F 1/00* (2006.01)

(56) References Cited

U.S. PATENT DOCUMENTS

| | | | |
|---|---|---|---|
| 3,144,341 A | | 8/1964 | Thompson et al. |
| 3,294,837 A | * | 12/1966 | Thompson ............... 560/185 |
| 3,929,678 A | | 12/1975 | Laughlin et al. |
| 4,199,483 A | | 4/1980 | Jones |
| 4,222,905 A | | 9/1980 | Cockrell, Jr. |
| 4,295,217 A | | 10/1981 | Fennel, Jr. et al. |
| 5,399,353 A | * | 3/1995 | Bartnik et al. ............ 424/438 |
| 5,618,850 A | * | 4/1997 | Coury et al. ............. 514/772.2 |
| 5,705,147 A | | 1/1998 | Shapiro et al. |
| 5,880,082 A | * | 3/1999 | Welch et al. ............. 510/365 |
| 5,891,836 A | * | 4/1999 | Kacher ...................... 510/237 |
| 6,297,350 B1 | * | 10/2001 | Kricheldorf et al. ....... 528/354 |
| 6,420,326 B1 | * | 7/2002 | Maile et al. ............... 510/181 |
| 6,448,214 B1 | * | 9/2002 | Del Duca et al. ......... 510/372 |
| 6,492,317 B1 | * | 12/2002 | Kerobo et al. ............ 510/421 |
| 6,630,569 B1 | * | 10/2003 | Jeschke et al. ............ 530/317 |
| 2005/0215453 A1 | | 9/2005 | Teissier |
| 2005/0240064 A1 | * | 10/2005 | Weerasooriya et al. ...... 568/679 |
| 2006/0149090 A1 | * | 7/2006 | Watanabe et al. ......... 556/437 |
| 2007/0238631 A1 | * | 10/2007 | Gambogi et al. .......... 510/237 |
| 2008/0287538 A1 | * | 11/2008 | Scholz et al. ............. 514/552 |

OTHER PUBLICATIONS

Office Action in U.S. Appl. No. 12/349,316, dated Aug. 2, 2010.
European Search Report corresponding to European Patent Application Serial No. 07812688.5-1211, dated Jul. 6, 2009.
Anon, "Alkyl lactyllactates and preparation and applications thereof." ip.com Journal, Mar. 22, 2007, XP002533919.
Rehberg et al., "Esters of Lactyllactic Acid." Journal of American Chemical Society, vol. 74, Mar. 20, 1952. XP001113148.
Kumar et al., "Poly(3-hydroxybutyrate)-depolymerase from *Pseudomonas lemoignei*: Catalysis of Esterifications in Organic Media." Journal of Organic Chemistry, vol. 65, No. 23, 2000. XP002533920.

* cited by examiner

ALKYL LACTYLLACTATE SOLVENT COMPOSITIONS

RELATED APPLICATIONS

This application is a continuation of International Application Serial No. PCT/US2007/072937 (International Publication No. WO 2008/006058 A3), having an International filing date of Jul. 6, 2007. This PCT application claims priority to U.S. provisional patent application Ser. No. 60/819,145, filed Jul. 6, 2006, Ser. No. 60/842,476, filed Sep. 6, 2006, and Ser. No. 60/896,205, filed Mar. 21, 2007. The entire specifications of the PCT and provisional applications referred to above are hereby incorporated by reference. This application is related to a co-pending application, Ser. No. 12/349,316 that is filed on the same as this application.

FEDERALLY SPONSORED RESEARCH OR DEVELOPMENT

[Not Applicable]

BACKGROUND OF THE INVENTION

The presently described technology relates generally to alkyl lactyllactate and alkoxylated alkyl lactyllactate compounds that can be used as solvents in a variety of applications. In particular, the alkyl lactyllactate and alkoxylated alkyl lactyllactate compounds, and compositions comprising or incorporating such compounds, are suitable for use in oil field applications, gypsum foamers, paints and coatings, adhesives, or other applications requiring the use of a solvent to, for example, improve cold tolerance performance (e.g., applications requiring cold weather performance without inclusion of additional volatile components) or effect the coalescent of a polymer film. The alkyl lactyllactate compounds of the present technology are also suitable for use in compositions for degreasing and stain removal.

Solvents are used in a wide variety of industrial applications. Success of the operation in which the solvent is used is highly dependent upon proper solvent selection. Thus, the characteristics of a solvent are an important consideration in determining whether a solvent will be suitable for a particular application. For many industrial processes, it is desirable that the solvent be non-hazardous, have low volatile organic compound (VOC) emissions, and have a high flash point. Other desirable characteristics, depending upon the end use, include the ability to control solvent polarity to enable the solvent to dissolve in oils and/or water, pour point depression, and support high loading of solids.

U.S. Pat. Nos. 2,350,388 and 2,371,281 (Claborn) (the "Claborn patents") generally describe that an alkyl lactyllactate can allegedly be produced by heating a mixture of a dry lactide and a desired anhydrous alcohol at a temperature of about from 70° to 90° C. for a period of about from 6 to 8 hours in the presence of an acid catalyst under anhydrous conditions. The Claborn patents also generally describe that alkyl lactyllactates have properties asserted to be desirable for solvents and plasticizers and also have properties that are said to be desirable for use in the preparation of other plasticizers.

The process to prepare alkyl lactyllactates as described in the Claborn patents, however, requires a solvent in the reaction mixture, which is either an excess amount of the alcohol or an inert organic liquid, such as benzene. The Claborn patents also require a reaction temperature of above 70° C. It is desirable, however, to eliminate the use of solvents in the reaction process and/or to have a process that can run at a lower reaction temperature. Further, the Claborn patents do not appreciate the effect of chirality of the alkyl lactyllactate on its properties and do not teach how to make alkyl lactyllactate with different chiralities. Nor do the Claborn patents appreciate the effects of the choice of alcohol (or another hydroxyl containing compound), and in particular the effects of alkoxylation, on the product yield, purity of the product, and properties of the product. It is desirable, however, to have a process that can produce a better yield of a higher purity alkyl lactyllactate product without distillation or other purification. It is also desirable to make and use an alkyl lactyllactate with a selected chirality to achieve or improve certain desired product properties.

U.S. Pat. No. 3,144,341 (Thompson) (the "Thompson patent") discloses stearyl lactyllactate and cetyl lactyllactate produced by reacting stearyl alcohol or cetyl alcohol with lactic acid. The stearyl lactyllactate and cetyl lactyllactate so produced are generally described as emulsifying agents particularly suitable as shortening addition agents in cake mixes and the like. The Thompson patent states that the reaction product is a mixture of stearyl lactyllactate and stearyl lactate, which are referred to as stearyl lactoyl lactate and stearyl lactate, respectively. Col. 3, lines 29-31. The Thompson patent further states that stearyl lactate is less effective than the desired stearyl lactyllactate. Col. 3, lines 56-57.

The reference recommends the use of 2.1 moles of lactic acid per one mole of stearyl alcohol (or cetyl alcohol), col. 1, lines 31-54, but suggests that the reaction of stearyl lactyllactate with an additional mole of lactic acid offered no appreciable advantages. Col. 3, lines 57-59. The Thompson patent also does not teach or suggest the use of a catalyst for the reaction of the alcohol with lactic acid. Because it is believed that alkyl lactyllactates are more efficient and can provide better performance and stability than alkyl lactates, it is desirable to have an improved process that can produce an alkyl lactyllactate product via a lactic acid route that contains a higher ratio of the lactyllactate component over the lactate component.

The alkyl lactyllactates and alkoxylated alkyl lactyllactates of the present technology can meet one or more of the above and other desirable attributes.

BRIEF SUMMARY OF THE INVENTION

In one aspect, the presently described technology provides a solvent composition comprising at least one alkyl lactyllactate having the following general structure:

Wherein R is an alkyl group, or an alkoxylated alkyl group, derived from a hydroxyl containing compound and comprises from about 1 to about 22 carbon atoms, alternatively from about 4 to about 10 carbon atoms, alternatively from about 6 to about 18 carbon atoms. Preferably, the alkyl lactyllactates of the present technology exhibit a specific chirality, which can be, for example, L-lactyllactate derived from an L-lactide or L-lactic acid source, D-lactyllactate derived from a D-lactide or D-lactic acid source; an L,D/D,L racemic lactyllactate made from, for example, meso-lactide, or an L,D/D,L racemic lactyllactate made from, for example, racemic lactide, or a mixture thereof. The solvent composition can be in an aqueous system or in other forms. Moreover, the composition can further comprise other components such as active components and, optionally, additional additives, such as, for example, solvents, buffers, surfactants, or other additives, depending upon the end use for the composition. In at least one embodiment, the alkyl lactyllactate composition exhibits the property of increasing fluidity at low temperature without significantly degrading performance properties such as foaming performance. Thus, in this aspect of the present technology, the alkyl lactyllactate compositions can be utilized in oil field applications, gypsum foamers, paints and coatings, adhesives or other applications requiring the use of a solvent to, for example, improve cold tolerance performance without inclusion of additional volatile components. In other embodiments, the alkyl lactyllactate composition exhibits the properties of soil solubilization, soil coupling, grease penetration, soil substrate modification and surface tension reduction. These properties enable at least some embodiments of the alkyl lactyllactate compositions to be utilized as degreasing compositions, stain, varnish and graffiti removal compositions, carpet spot cleaners, and waterless hand cleaners.

DETAILED DESCRIPTION OF THE INVENTION

In accordance with some embodiments, the alkyl lactyllactates of the present technology can be of the following general structure (I):

(I)

In general structure (I), R comprises an alkyl group or alkoxylated alkyl group derived from a hydroxyl containing compound having either mono or plural hydroxyl groups. The alkyl lactyllactates can be prepared from a lactide and a hydroxyl containing compound or an alkoxylated hydroxyl containing compound. The alkyl lactyllactates can also be prepared directly from a lactic acid. Preferably, the lactic acid used to prepare the lactide or the alkyl lactyllactates of the present technology is produced via a fermentation method. Further disclosure of the processes for preparing the alkyl lactyllactylates of the present technology can be found in co-pending application docket no. 17730WO01 assigned to Stepan Company, which disclosure is hereby incorporated by reference in its entirety.

The reaction temperatures for producing alkyl lactyllactates of the present technology can be in the range of from about 15° C. to about 150° C., alternatively from about 20° C. to about 100° C., alternatively from about 25° C. to about 75° C., alternatively from about 30° C. to about 70° C. In accordance with at least some embodiments (e.g., to make alkyl lactyllactates for solvency applications), the reaction temperature preferably is in the range of from about 40° C. to about 60° C., alternatively from about 40° C. to about 50° C.

An acid catalyst is preferably used in the reaction of lactide and alcohol (i.e., a hydroxyl containing compound). Examples of acid catalysts include, but are not limited to, $H_2SO_4$, HCl, p-toluenesulfonic acid (pTSA), and Nafion® ionomers (sulfonated tetrafluoroethylene copolymers, CAS No. 31175-20-9, available from E.I. du Pont de Nemours and Company). In accordance with at least some embodiments, the amount of catalyst needed for one or more processes of the present technology is about 1.0 wt % or less, alternatively from about 0.01 wt % to about 0.4 wt %, based on the weight of lactide in the reaction mixture.

It has been discovered that the processes of the presently described technology can substantially reduce or avoid the production of by-products and unexpectedly increase the production yield and product purity of the targeted alkyl lactyllactate. For example, it has been discovered that the reaction of lactide with an alcohol (e.g., L-lactide with lauryl alcohol) in accordance with the present technology can achieve a yield of about 95% or more, and the purity of alkyl lactyllactate in the product mixture without further purification can reach about 90% to about 95%. The amount of alkyl lactate by-product or remaining alcohol is preferably less than about 5%, for example, in the range of from about 1% to about 5%.

In accordance with at least one embodiment of the present technology, equivalent moles of lactide, e.g., solid L-lactide, and a fatty alcohol are combined at an elevated temperature (e.g., 50° C.) with a catalytic amount (approximately about 0.01% to about 1% by weight based on the weight of the lactide) of sulfuric acid. Different molar ratios of lactide and alcohol, for example, an excess amount of lactide or alcohol(s), can be used. However, equivalent amounts of lactide and alcohol(s) are preferred for at least some embodiments of the present technology. The reaction stops after approximately 12 to 24 hours (e.g., approximately 16 hours) when the mixture becomes a hazy to clear, homogeneous liquid, preferably a clear homogeneous liquid. If the mixture is hazy, then the mixture can be heated at an elevated temperature (e.g., 50-60° C.) for an extended period of time to generate the preferred clear, homogeneous liquid. Generally, the lower the reaction temperature, the longer the reaction time is needed. The mixture can be used in solvent and other applications (e.g., personal care, home care and industrial cleansing applications). The residual sulfuric acid can be left in, or removed by, for example, water washing, adsorption onto basic alumina or silica media, or via neutralization with a base.

In accordance with at least one other embodiment of the present technology, a lactide and a hydroxyl containing compound with two or more hydroxyl groups can be condensed in at least a 1:1 or higher molar ratio to make the alkyl lactyllactate of the present technology. The hydroxyl containing compound can be a fatty alcohol or alkoxylated alcohol, and can be a polyol or alkoxylated polyol containing two or more hydroxyl groups, preferably two or more primary hydroxyl groups. Alternatively, an excess amount of alcohol or lactide can be used. For example, use of an excess of ethoxylated alcohol to form the alkyl lactyllactate could help in emulsification. This could be accomplished in two ways: first, the exact 1:1 alkyl lactyllactate is made, then excess alcohol is added, or two, the alcohol could be added up front and the alkyl lactyllactate is made in one step. This could improve the reaction speed by using up all of the lactide faster.

Alternatively, alkyl lactyllactates of the present technology can be made from lactic acid (e.g., L-lactic acid, D-lactic acid, or racemic lactic acid) and a hydroxyl containing compound such as an alcohol. The reaction product is normally a mixture of alkyl lactyllactate(s) and alkyl lactate(s). The presently described technology provides improved processes for making alkyl lactyllactates using lactic acid. It has been found that a reaction product produced by one or more of the reaction processes of the present technology has an unexpectedly increased ratio of alkyl lactyllactate(s) over alkyl lactate(s) than can be achieved by processes of the prior art.

The lactic acid process of the present technology differs from the prior art in, for example, that a catalyst (e.g., para-toluenesulfonic acid) is used and/or a higher ratio of lactic acid to alcohol is used. These two reaction variables can increase the amount of alkyl lactyllactate(s) (e.g., lauryl lactyllactate (L3)) produced in the reaction, and decrease the amount of alkyl lactate(s) (e.g., lauryl lactate (L2)) produced. Examples of catalysts that can be used include, but are not limited to, sulfuric acid ($H_2SO_4$), HCl, methanesulfonic acid, $BF_3$ etherate, para-toluenesulfonic (pTSA), phosphoric acid, and Nafion® ionomers. Methanesulfonic acid, $BF_3$ etherate, and pTSA are preferred. In at least one embodiment, pTSA is most preferred. Preferably, at least about four equivalents, alternatively at least about six equivalents, alternatively at least about eight equivalents, of lactic acid per one equivalent of alcohol (e.g., a fatty alcohol) are used.

L-lactic acid is preferred at least for some applications (such as solvent applications) of the present technology, but D-lactic acid or racemic lactic acid can also be used. Preferably, the lactic acid is made by a fermentation process. The reaction temperature of the lactic acid process is preferably in the range of from about 120° C. to about 200° C., alternatively from about 140° C. to about 165° C., alternatively from about 180° C. to about 185° C.

The alkyl lactyllactate composition obtained using the lactic acid process of the present technology is different from alkyl lactyllactate compositions obtained in the lactic acid processes of the prior art, for example, U.S. Pat. No. 3,144,341, and contain substantially more lactyllactate content. For example, the reaction products produced from the lactic acid process described in U.S. Pat. No. 3,144,341 only contain about 20% or less alkyl lactyllactates, while the reaction products of the lactic acid process of the present technology can contain at least about 40%, alternatively at least about 50% alkyl lactyllactates, based on the total weight of lactyllactate and lactate in the reaction product. The alkyl lactyllactates produced by the lactic acid processes of the present technology can exhibit different and/or superior properties than the alkyl lactyllactate compositions produced by the lactic acid processes of the prior art.

For some solvency applications it may be desirable that the alkyl lactyllactate have a specific chirality, which can be, for example, an L-lactyllactate, a D-lactyllactate, an L,D/D,L racemic lactyllactate made from, for example, meso-lactide or an L,L/D,D racemic lactyllactate made from, for example, racemic lactide or a mixture thereof. Thus, the alkyl lactyllactate of the present technology can be in different forms depending upon the starting materials. For example, it can be a chiral lactyllactate made by reacting a chiral lactide (L- or D-lactide) with an alcohol, a racemic lactyllactate made by reacting meso lactide or racemic lactide with an alcohol, a mixture of alkyl lactyllactates made by reacting a mixture of L-lactide and meso-lactide with an alcohol, and a mixture of alkyl lactate and alkyl lactyllactate by reacting a lactic acid with an alcohol using the processes of the present technology.

Additionally, at least some of the preferred alkyl lactyllactate compounds of the present technology are a clear, colorless liquid, and are nitrogen free, salt free and 100% active. The alkyl lactyllactates may also be naturally derived. Preferably, the alkyl lactyllactates can be formulated in cold-mix applications.

Alternatively, an alkyl lactyllactate of the present technology can be a mixture of alkyl lactyllactate(s) and alkyl lactate(s) produced by the reaction processes of the present technology. Preferably, this mixture has a lactyllactate to lactate molar ratio of greater than about 0.5:1, more preferably greater than about 0.8:1, most preferably greater than about 1:1 (e.g., about 1.4:1).

The hydroxyl containing compound can be straight, branched, saturated, or unsaturated, and can be derived from natural or synthetic feed stocks. The alkyl group in the hydroxyl containing compound can include from about 1 to about 22, alternatively from about 4 to about 18 carbon atoms. Suitable hydroxyl containing compounds for use in forming the alkyl lactyllactates include, for example, alcohols, TMP, TMP ethoxylates, pentaerythritol, pentaerythritol ethoxylates, and hydroxy stearic compounds.

As a result, the alcohol (i.e., an example of a hydroxyl containing compound suitable for use in the practice of the present technology) preferably contains at least one primary hydroxyl group. More preferably, the alcohol is a fatty alcohol containing from about 6 to about 18 carbon atoms, alternatively about 12 to about 18 carbon atoms. Additionally, alcohols as introduced above, including primary, secondary, or tertiary alcohols, can be utilized to react with the lactic acid or lactide. It has been discovered that at least in some embodiments, the ratio of alkyl lactyllactate(s) vs. alkyl lactate(s) in the reaction product can be improved by utilizing a primary alcohol. Similar to the lactide processes described above, preferably, no solvent is employed in a process using lactic acid to produce the alkyl lactyllactate of the present technology. It is an objective of the present technology to eliminate the use of a solvent in the reaction process. Typically, however, a solvent free process can be difficult to operate because of viscosity or product distribution concerns. It has been surprisingly found that a reaction product with the desired lactyllactate to lactate or higher polymer distribution can be obtained without solvent. The alkyl lactyllactate product produced by the lactide processes of the present technology preferably contains more than about 90% of at least one alkyl lactyllactate and less than about 10% of alkyl lactate(s), higher polymer(s) and other impurities based on the total weight of the reaction product using a solvent-free reaction system.

The hydroxyl containing compounds of the present technology may be alkoxylated, for example, hydroxyl containing compounds that are ethoxylated, propoxylated or both. The hydroxyl containing compounds can be alkoxylated in situ when reacting with lactide. Alternatively, preformed alkoxylated hydroxyl containing compounds can be used. For example, ethoxylated lauryl alcohols can be used to produce ethoxylated lauryl lactyllactates (LLL(EO)) containing a specific amount (e.g., 1 mole, 2 moles, or 3 moles) of ethoxylate (EO) per mole of the lactyllactate (e.g., LLL (1EO), LLL (2EO), or LLL (3EO)). Alkoxylation improves the water solubility and compatibility of the alkyl lactyllactates with other polar materials which may be in a formulation.

In accordance with some embodiments, the alkyl lactyllactate of the present technology can be represented by the following general structure (II):

(II)

In the general structure (II), R contains about two to about six, preferably about two to about three carbon atoms, $R^1$ contains about one to about twenty two, alternatively about one to about eighteen, alternatively about four to about eighteen, alternatively about twelve to about fourteen, alternatively about one to about six carbon atoms (e.g., four carbon atoms), and the number of repeat units (n) can vary from about 1 to about 100. In order to minimize VOC emissions, R, $R^1$ and n are preferably selected such that the general structure (II) alkyl lactyllactate has at least twelve carbon atoms. For example, R has two carbon atoms, n is 1 and $R^1$ has four carbon atoms (e.g., butanol+1 EO), alternatively, R has two carbon atoms, n is 2 and $R^1$ has four carbon atoms (e.g., butanol+2EO), alternatively R has two carbon atoms, n is 2 and $R^1$ has two carbon atoms (e.g., ethanol+2EO), alternatively R has two carbon atoms, n is 2 and $R^1$ has six carbon atoms (e.g., hexanol+2EO).

In some embodiments, the R group in the general structure (I) or $R^1$ group in the general structure (II) above can be derived from a diol with two primary hydroxyl groups (OH's) or a polyol containing two or more primary OH's. In some other embodiments, the R group can be derived from diols or polyols containing at least one primary OH. For example, when a compound containing two primary hydroxyl groups (e.g., glycerin or ethoxylated glycerin) is used as the bridging molecule, the alkyl lactyllactate in accordance with some embodiments of the present technology can be represented by the following general structure (III):

(III)

In accordance with these embodiments, n is from about 1 to about 100, and the R group in the above formula (III) is H, an aliphatic or an aromatic containing hydrocarbon. Preferably, the R group is H or a linear hydrocarbon containing from about one to about eight carbon atoms, and n is from about 1 to about 26. When a compound containing two or more hydroxyl groups is used as the bridging molecule, the alkyl lactyllactate can be represented by the following general structure (IV):

(IV)

In general structure (IV), $R^1$ is H, an aliphatic or an aromatic containing hydrocarbon group, R is a polyhydridic aliphatic or aromatic hydrocarbon, n is from one to about 100, and x is from 1 to the total number of hydroxyls present. Preferably, $R^1$ is H or a linear hydrocarbon containing one to eight carbon atoms, and n is from about 1 to about 26.

The alkoxylated alkyl lactyllactates of the present technology have been found to be desirable solvents for oilfield applications (e.g., enhanced oil recovery (EOR) completion fluids, production enhancement fluids, flow assurance chemicals, or gas well unloading) and gypsum foaming applications. At least some alkyl lactyllactates of the present technology can function as solvents in a wide variety of applications and display advantages over conventional solvents such as water, alcohols, short-chain ethers and esters, aliphatic and aromatic hydrocarbons. The advantages of using alkyl lactylates as solvents in these applications arise from one or more of the following properties:

Ability to control solvent polarity. Because the polarity of an alkyl lactyllactate is determined principally by the ester group, and because a wide variety of hydroxyl containing compounds can be utilized to esterify the lactide, the polarity of an alkyl lactyllactate solvent can be readily tuned to suit a particular application. For instance, if the alkyl lactyllactate is required to be miscible with water, one could choose an alcohol that has a short alkyl chain or an alcohol-ether with a high degree of ethoxylation to esterify the lactide. On the other hand, if the application in question required a water-insoluble solvent, the hydrophobe length of the alkyl group could be increased and/or the degree of ethoxylation could be decreased. These changes can be made almost continuously, giving the formulator a great control over the solvent properties.

Low Volatile Organic Compound (VOC) Content. At least some alkyl lactyllactates of the present technology, especially those based on ethoxylated hydroxyl containing compounds, have high molecular weights compared to conventional solvents. This provides an advantage over conventional solvents, as they are considered a VOC component due to their volatility.

High Flash-Point. Related to the vapor pressure of alkyl lactyllactates is the ability to make alkyl lactyllactate solvents that are considered high-flashpoint compared to conventional solvents such as isopropyl alcohol and ethanol. At least some alkyl lactyllactates of the present technology have relatively higher flash points compared to isopropyl alcohol and ethanol.

Product Handling properties. At least some alkyl lactyllactates of the present technology have the ability to reduce pour point, the ability to re-constitute a material after freezing without heating or the need for agitation in order to obtain a homogeneous composition (e.g., freeze/thaw stability), the ability to increase loading of actives (with the same handling properties), and the ability to reduce gelling when a high actives composition is diluted to a low actives composition, for use in colder temperatures.

Alkyl lactyllactates can potentially be used in virtually any application that requires a low-volatility solvent. For example, some alkyl lactyllactates of the present technology, especially some alkoxylated alkyl lactyllactates, have been found to be desirable solvents for oilfield applications and gypsum foaming applications. Surprisingly, the alkoxylated lactyllactate ester compositions of the present technology exhibit depressed pour point temperatures, remain homogeneous after being frozen and subsequently thawed without agitation, and can be used to increase fluidity at low temperatures without significantly degrading performance properties such as foaming performance. For example, alkyl ether sulfates such as Alpha Foamer® products, available from the STEPAN company, can exhibit a relatively high pour point (e.g., about −20° C.) when used alone. However, these foaming agents can be improved by the alkoxylated lactyllactate esters of the present technology (e.g., 25% diethylene glycol monobutylether lactyllactate ester prepared from, for example, Butyl Carbitol™ available from Dow Chemical Company, Midland, Mich.) to have a much lower pour point, for example lower than about −25° C., alternatively lower than about −35° C., alternatively lower than about −45° C., alternatively as low as about −50° C. or lower. Such alkoxylated alkyl lactyllactates can be used to make ether sulfate products that contain 40% or more actives (e.g., C6-10 ether sulfates), alternatively 60% or more actives, and the ether sulfate products can be diluted in water to dilutions of about 1% or less with no or little gelling. These properties are significant in that the alkyl lactyllactate compositions of the present technology can provide cold tolerance performance (e.g., a depressed pour point) in applications that preferably do not utilize further volatile and/or flammable components such as oil field applications (e.g., gas-well unloading an enhanced oil recovery), gypsum foaming applications, paints and coatings (e.g., flow and leveling aides, coalescing agents, and anti-freeze additives), adhesives (e.g., application aids and wetting agents), de-icing fluids, anti-freeze for engines, hydraulic fluids, etc. In addition to reduced pour points, at least some alkyl lactyllactates of the present technology have increased flashpoints compared to conventional solvents such as ethanol or isopropyl alcohol. The alkyl lactyllactates have flash points of about 100° F. or higher, alternatively about 140° F. or higher, alternatively about 200° F. or higher, alternatively about 500° F. or higher.

As another example, at least some alkoxylated alkyl lactyllactates can be used as additives to oilfield completion fluids. Completion fluids are fluids that are circulated through a well before production starts. They are used to remove the drilling fluids and contaminants left behind from the drilling operation that may cause problems once the well is brought into production. Such fluids can be, for example, water, brines, and oils, such as olefins or kerosene. The alkyl lactyllactate and alkyl ethoxy lactyllactate compounds can be added to these various completion fluids to aid in the removal of the contaminants. Because the contaminants are removed more readily when the alkyl lactyllactate is added to the completion fluid, less of the completion fluid is needed to remove the contaminants, thereby reducing costs and the environmental impact of the use of the completion fluid. It has been discovered that when mixed with either olefin or kerosene, at least some alkoxylated alkyl lactyllactates of the present technology (e.g., diethylene glycol monobutyl ether lactyllactate) are soluble, and when added to oilfield completion fluids in a sufficient amount (e.g., at 10% or more), allow the completion fluids to be washed off with water or brine more easily.

Further, it has been surprisingly discovered that some alkyl lactyllactates of the present technology (e.g., 2 ethyl hexanol+2EO lactyllactate, 2-EH-2EO LL) can dissolve tar/asphalt. Therefore, it is expected that at least some alkyl lactyllactates and alkoxylated alkyl lactyllactates can be useful in cleaning oil pipeline clogged with asphaltenes and/or paraffins, for example.

In addition to the gypsum foamer and oilfield applications discussed above, the alkyl lactyllactate solvents of the present technology can be used in the following areas: coalescing agents in paints and coatings; anti-freeze agents in paints and coatings; rheology modifiers in paints and coatings; wetting agents in paints and coatings; rheology modifiers in pressure sensitive adhesives; wetting agents in pressure sensitive adhesives; de-icing agents for vehicles and buildings; hydraulic fluids; and solvents for agricultural applications.

For example, the alkyl lactyllactates can be used as a coalescing agent for polymer films. Typically in this application, an agent is added to the polymer suspension which can adjust the minimum film-forming temperature (MFFT) of the polymer to an appropriate value (i.e., below the application temperature). If a polymer is applied below the MFFT, the resulting film is usually rough and shows poor adhesion to the substrate, presumably because the polymer particles do not intermingle or conform to the surface. Application of a polymer above the MFFT results in a smooth film with enhanced adhesion to the surface. Coalescing agents are believed to function by solvating the polymer, reducing the apparent glass transition temperature, and allowing polymer chains to intermingle and conform to the substrate. It is important that the coalescing agent have the right interactions with the polymer in order to provide the lower glass transition temperature.

An example of a commercially important coalescing agent for paints and coatings is 2,2,4-trimethyl-1,3-pentanediol monoisobutyrate (TEXANOL® ester alcohol). However, many commercial coalescing agents are under regulatory scrutiny owing to their organic composition and their volatile nature. The alkyl lactyllactate of the present technology have reduced volatility compared to solvents with lower molecular weight. By adjusting the identity of the R group and the alkoxy content of the alkyl lactyllactates, it is possible to tailor the interactions between the alkyl lactyllactates and the polymer, producing a relatively low-volatility coalescing agent.

At least some embodiments of the alkyl lactyllactates of the present technology can also be used as solvents for stain removal and degreasing applications. For example, at least some alkyl lactyllactates can be used as solvents to make a liquid graffiti remover, a varnish remover, a carbon mark remover, or a heavy duty cleaner/degreaser. The alkyl lactyllactates are used in such removers in an amount of from about 1% to about 80%, alternatively from about 5% to about 50%, alternatively about 10% to about 50%, alternatively from about 20% to about 30% actives all based on the total weight of the remover.

Other ingredients, such as soya methyl ester, in amounts of about 0 to about 50%, alternatively, about 0% to about 40%, alternatively of about 0% to about 30% ethyl lactate in amounts of about 0% to about 50%, alternatively about 0% to about 30% and/or d-limonene in amounts of about 0 to about 50%, alternatively about 5% to about 45%, can be used in such remover compositions in combination with the alkyl lactyllactates of the present technology. Other ingredients such as alcohol ethoxylates, short chain alcohols (e.g., ethanol, IPA, etc.), and/or alkanolamide can also be used in proper amounts as known in the art, depending upon the desired end use for the solvent composition.

In accordance with another embodiment, the alkyl lactyllactate of the present technology is used as a solvent in carpet traffic spotter/pretreatment compositions. Suitable amounts of the alkyl lactyllactate in such compositions range from about 1 to about 8%, alternatively about 1% to about 5%, alternatively about 1% to about 4% by weight of the total weight of the composition. Other components in the composition can be for example, glycol ethers in amounts ranging from about 0 to about 8%, alternatively about 1 to about 4%; alcohol sulfates in amounts ranging from about 0.1 to about 5%, alternatively about 1% to about 4%; amine oxides in amounts ranging from about 0.1 to about 2%, alternatively about 0.1 to about 1%, all in amounts by weight of the total composition, with the balance being water.

In accordance with another embodiment, the alkyl lactyllactate of the present technology is used as a solvent to formulate an animal fat degreaser/grease trap cleaner in the amount of, for example, from about 5% to about 50%, alternatively from about 5% to about 35% actives, based on the total weight of the cleaner, in combination with other ingredients such as, for example, ethyl lactate, soya methyl ester, alcohol ethoxylate, and d-limonene.

In accordance with yet another embodiment, the alkyl lactyllactate of the present technology can be used to formulate a waterless hand cleaner in an amount of, for example, from about 5% to about 30%, alternatively from about 10% to about 25% actives, alternatively, about 15% to about 20%, actives, in combination with, for example, about 40% to about 60% of water; or a thick gel waterless hand cleaner in an amount of, for example, from about 1% to about 80%, alternatively about 5% to about 50%, alternatively about 10% to about 25% actives, based on the total weight of the cleaner, in combination with other solvents and wetting agents, and without added water.

The alkyl lactyllactates of the present technology are combined with an active component and, optionally at least one additive to prepare the solvent compositions that are used in, for example, oil field applications, gypsum foaming applications, paints, coatings and adhesives. The active component can be an alkyl ether sulfate comprising from about six to about 10 carbon atoms, or a salt thereof. Other examples of active components include betaines (e.g., AMPHOSOL® DM, AMPHOSOL® GC available from Stepan Company), sulfobetaines (e.g., AMPHOSOL® CS-50 available from Stepan Company), and alkyl sulfates (e.g., sodium lauryl sulfate, STEPANOL® WAC available from Stepan Company). The active component is present in the composition in an amount of about 35% or more actives, alternatively about 40% or more actives, alternatively about 50% or more actives, alternatively about 60% or more actives.

Additionally, one or more solvent compositions comprising the alkyl lactyllactate of the present technology can optionally contain at least one or more other additives, including organic or inorganic surfactants such as anionic, cationic, nonionic, amphoteric and zwitterionic surfactants, derivatives thereof, or mixtures thereof. These surfactants are known in the art, and are described in, for example, U.S. Pat. No. 3,929,678 (Laughlin et al.), which is incorporated herein by reference. Examples of useful cationic surfactants also include those described in U.S. Pat. No. 4,295,217 (Murphy) and U.S. Pat. No. 4,222,905 (Cockrell), both of which are incorporated herein by reference. In accordance with some embodiments, the one or more other surfactants in a solvent composition can represent from about 1% to about 95%, preferably from about 2% to about 70%, more preferably from about 2% to about 30%, alternatively from about 3% to about 10%, by weight of the cleansing composition.

Examples of popular nonionic surfactants for use with the present technology include, but are not limited to, alkyl phenol ethoxylates, alcohol alkoxylates C8-18 EO 2-12, alkyl dimethyl or alkyl amido propyl dimethyl amine oxides, MEA or DEA type alkanolamide, alkyl polyglycoside, ethoxylated alkanolamides, and mixtures thereof. For heavy duty cleaners/removers, alcohol ethoxylate or alkanolamide are preferred examples of nonionic surfactants. Examples of anionic surfactants include, but are not limited to, alcohol sulfates, alcohol alkyoxylated sulfates, alkylbenzene sulfonates, fatty acid soaps, and mixtures thereof. Examples of amphoteric surfactants include, but are not limited to, sultaines, betaines, alkyl dimethyl or alkyl amido propyl dimethyl betaines, alkyl dimethyl or alkyl amido, propyl dimethyl amine oxides, mono- or di-sodium alkyl ampho (mono- or di)acetates; proprionates, sarcosinates, and mixtures thereof. Examples of quaternary ammonium compounds (quats) that can be used in combination with the alkyl lactyllactates of the present technology include, but are not limited to, dialkyl dimethyl ammonium chlorides, alkyl dimethyl benzyl/ethyl benzyl ammonium chlorides, alkyl dimethyl benzyl ammonium chlorides, and mixtures thereof.

Anionic and zwitterionic surfactants can also be used in combination with the alkyl lactyllactates of the present technology. Useful anionic surfactants specifically include those described in U.S. Pat. No. 3,929,678 (Laughllin et al.) and those described in U.S. Pat. No. 4,199,483 (Jones), which are incorporated herein by reference.

Other optional additives, particularly for use in preparing compositions for stain removal or degreasing include soya methyl ester, ethyl lactate, d-limonene, alkanolamides, short chain alcohols, and derivatives thereof.

In accordance with at least one embodiment of the present technology, a composition comprising an alkyl lactyllactate of the present technology and a surfactant in an aqueous system can further comprise a buffer to improve the performance of the composition. Any surfactants and buffering agents can be used. Examples of buffering systems include a citric acid/sodium citrate buffer, a lactic acid/ammonium lactate buffer, or a combination thereof. For solvency applications, each surfactant system can require a different buffer system with a different concentration. The proper amount of the buffer needed can be determined by routine experiments and is dependent on the level of lactyllactate and other actives used in a formulation. In general, the level of the buffer can be in the range of from about 0 to about 1%, alternatively from about 0.1% to about 0.75%, alternatively from about 0.1% to about 0.5%, based on the weight of the formulation.

The presently described technology and its advantages will be better understood by reference to the following examples. These examples are provided to describe specific embodiments of the present technology. By providing these specific examples, the applicants do not limit the scope and spirit of the present technology. It will be understood by those skilled in the art that the full scope of the presently described technology encompasses the subject matter defined by the claims appending this specification and any alterations, modifications, or equivalents of those claims.

EXAMPLE 1

Preparation of a Lactyllactate Ester Using Lactide and Butyl Carbitol™

In a 200 ml round bottom flask, 56.28 grams of Butyl Carbitol™, (diethylene glycol monobutyl ether), available from Dow Chemical Co., was mixed with 50.0 grams of lactide. After mixing, 2 drops of concentrated sulfuric acid were added. A stopper was added to the top of the flask, and the flask was closed. The flask was then placed in an oven at 60° C. overnight. The resultant product produced was a butyl carbitol/lactide ester (1:1 mole ratio ester based upon the weight of the butyl carbitol and lactide utilized) having an average molecular weight of 306 (butyl carbitol molecular weight 162.23, lactic acid molecular weight 144.13). The butyl carbitol/lactide ester produced visually appeared to be slightly hazy. However, after heating on a hot plate at 55° C. with agitation and reflux for a period of 4 hours and subsequent cooling, the product appeared clear. Thus, it was determined that a clear lactyllactate ester can be produced from lactide and Butyl Carbitol™.

EXAMPLE 2

Use of Diethyleneglycol Monobutylether-based Lactyllactate Esters to Prepare a 60% Alkyl Ether Sulfate Sample An alkyl ether sulfate sample was prepared by adding 25% by weight diethyleneglycol monobutyl ether lactyllactate (Agent 2859-95) and 16% by weight water to a C8-10+2EO ether sulfate to arrive at a 59% actives ether sulfate lactyllactate ester product (Formulation 1). Formulation 1 was compared against a commercial foaming agent containing a C8-10+2EO ether sulfate at 59% actives in ethanol/water (15%/26%) (Comparative Formulation) in terms of foaming, pour point and flash point. The formulations are provided below in Table 1:

TABLE 1

| Formulation 1 | Grams | % by weight actives |
|---|---|---|
| C8-10 + 2EO ether sulfate (dried to 79% solids) | 74.68 | 59 |
| Agent 2859-95 (Butyl carbitol based lactyllactate) | 25.00 | 25 |
| Water | .32 | 16 |
| (total) | 100 g | 100 |

| Comparative Formulation | % by weight active |
|---|---|
| C8-10 2EO ether sulfate | 59 |
| Ethanol | 15 |
| Water | 26 |
| (total) | 100 |

The Comparative Formulation is flammable, has a pour point of −15° C. and the ethanol portion of the product is VOC. By comparison, Formulation 1 has a flash point of greater than 200° F., is non-flammable, non-VOC, has instantaneous cold water solubility and has a pour point of −5° C. The results show that Formulation 1 exhibited good cold performance capability without the need to use flammable, VOC solvents such as ethanol.

Formulation 1 was also foam performance tested against the Comparative Formulation using the following foam test.

Foam Test 1 liter of test solution is prepared by adding the required grams of surfactant, to achieve the desired concentration, to a 2 liter flask.

Water is added to 1000 g.

103 g of the test solution is added to the cup of a Hamilton Beach mixer.

A 1000 ml Cylinder is placed on the scale and tared.

The test solution in the cup is then mixed on high speed for 30 seconds.

The time for a stiff foam to develop is recorded. This is referred to as the "quick foam" time.

The foam generated is poured into the 1000 ml cylinder until 100 g has been poured in. The timer is started. The foam volume is recorded in cc's, and the foam stability is recorded as the time when 50 ml has separated.

Table 2 below provides the results of such a foam performance test.

TABLE 2

| | Formulation 1 | Comparative |
|---|---|---|
| Foam Quick Time | 5 seconds | 3 seconds |
| Foam Volume | 520 cc | 530 cc |
| Foam ½ Life | 249 seconds | 268 seconds |

As can be seen in Table 2, the foam performance for Formulation 1 was approximately that of the comparative formulation. Thus, the lactyllactate ester of the present technology exhibited foaming performance approximately equal to that of a conventional foaming agent alone. These results demonstrate that Formulation 1 and other lactyllactate esters of the present technology could be utilized in applications where cold storage performance, cold weather solubility performance, increased flashpoint performance and excellent foaming performance are desired—such as in the oil field arena where undesired flammable solvents are currently utilized. Moreover, it is also envisaged that other alcohol ethoxylates could also be used to prepare the lactyllactate esters of the present technology, such as, for example, ethyl glycol monobutyl ether, propylene glycol monobutyl ether, dipropylene glycol monomethyl ether, diethylene glycol mono (2-ethylhexyether), and combinations thereof.

EXAMPLE 3

Preparation of Glycerol Lactyllactate Ester

A sample of glycerol lactyllactate ester was made and the sample was further evaluated for use as a water soluble solvent for anionics. Based upon the molecular weight of glycerin (92.0) and lactide (144.13), the formulation of the glycerol lactyllactate ester included 75.80% lactide and 24.20% glycerin. To prepare the lactyllactate ester, 50 grams of lactide and 15.96 grams of glycerin were added to a round bottom flask and subsequently mixed. Then, 3 drops of sulfuric acid was added to the mixture and heat applied at a temperature of 50° F. on total reflux. The resultant glycerol lactyllactate ester exhibited a pour point of approximately 70° F. and was water soluble.

The sample of glycerol lactyllactate ester (25% ester content) was then mixed with an alkyl ether sulfate composition (88% actives) and water to produce a 60% actives final product. The product was visually observed and gelling was noted, but later the product became fluidized. Additionally, when placed within a freezer, the final product became solidified within approximately 2 minutes.

Finally, the final product was also evaluated for foam performance using the foam test described above. The quick foam time was approximately 4 seconds while the foam volume and foam ½ life were 495 cc and 236 cc, respectively. It was determined that the foam performance for the final product was good, but pour point performance could be improved through use of alkoxylation (e.g., ethoxylating the glycerin to improve pour point performance). A sample of ethoxylated glycerin G-26(26EO) was used to prepare a lactyllactate solvent (Solvent 3304-25). Pour point analysis showed the ethoxylated glycerin lactyllactate solvent had a pour point of −2° F. by the freezer method and −15.4° F. (−26.3° C.) by instrument. The solvent was then used to prepare a 60% active ether sulfate. This is a 60% active ether sulfate with 20% Solvent 3304-25 and 20% water as the solvent system. The product was clear and fluid at room temperature, diluted readily in water and has a pour point of 37.2° F. (2.9° C.) when measured in accordance with ASTM D97-02.

EXAMPLE 4

Evaluation of Lactyllactate Esters as Completion Fluids

Four lactyllactate esters were prepared for evaluation as completion fluid solvents: a glyceryl lactyllactate, a diethylene glycol monobutyl ether lactyllactate (C4-2LL), an isobutyl lactyllactate (C4 LL) and an octyl lactyllactate (C8 LL). Each of the lactyllactate esters was combined with a C16/18 olefin oil in amounts of 10% or 20% by weight and evaluated in accordance with the following test:

The surface of a carbon steel metal plate is wet with C16/18 olefin oil until the surface is oil wet. Then, using a funnel with a ½ inch opening, completion brine (25% $CaCl_2$) is poured over the surface of the plate at a 45° angle until the plate turns from oil to water wet. The lower the amount of grams of brine needed to water wet the plate, the better the performance of the completion fluid.

The results of the completion fluid test are shown in Table 3 below:

TABLE 3

|  | A | B | C | D | E | F | G |
|---|---|---|---|---|---|---|---|
| C16/18 Olefin | 100 | 90 | 90 | 90 | 90 | 80 | 80 |
| Glycerin LL |  | 10 |  |  |  | 20 |  |
| C4-2LL |  |  | 10 |  |  |  | 20 |
| C4 LL |  |  |  | 10 |  |  |  |
| C8 LL |  |  |  |  | 10 |  |  |
| g of 25% $CaCl_2$ | >500 | 425 | 310 | 450 | 400 | 400 | 220 |

From the Table 3 results, it can be seen that it took less completion brine to water wet the steel plate when the lactyllactate esters were added to the C16/18 olefin, and that the best results were obtained when the diethylene glycol monobutyl ether lactyllactate was added to the C16/18 olefin. Thus, the addition of lactyllactate esters to completion fluids can reduce the amount of completion fluid needed, thereby reducing costs as well as the environmental impact of the drilling operation.

EXAMPLE 5

Evaluation of Diethyleneglycol Monobutyl Ether Lactyllactate as a Solvent for Ether Sulfate Foaming Agent A C8-10+1EO ether sulfate ammonium salt sample was prepared by mixing 20% by weight of diethyleneglycol monobutyl ether lactyllactate with 61% by weight of the C8-10+1EO ether sulfate ammonium salt (dried to 85% active) and 19% by weight water. The product was clear and fluid at room temperature, demonstrating that the lactyllactate can function as a non-VOC solvent for ether sulfate foaming agents.

The ether sulfate ammonium salt sample containing the diethyleneglycol monobutyl ether lactyllactate was evaluated for foam performance using the foam test described above and compared with the foam performance of an ether sulfate ammonium salt sample containing a conventional ethanol solvent. The foam performance of the two samples at different concentrations in 342 ppm water is shown in the bar graph of FIG. 1 and the foam stability of the two samples at different concentrations is shown in the bar graph of FIG. 2.

Figure 1:
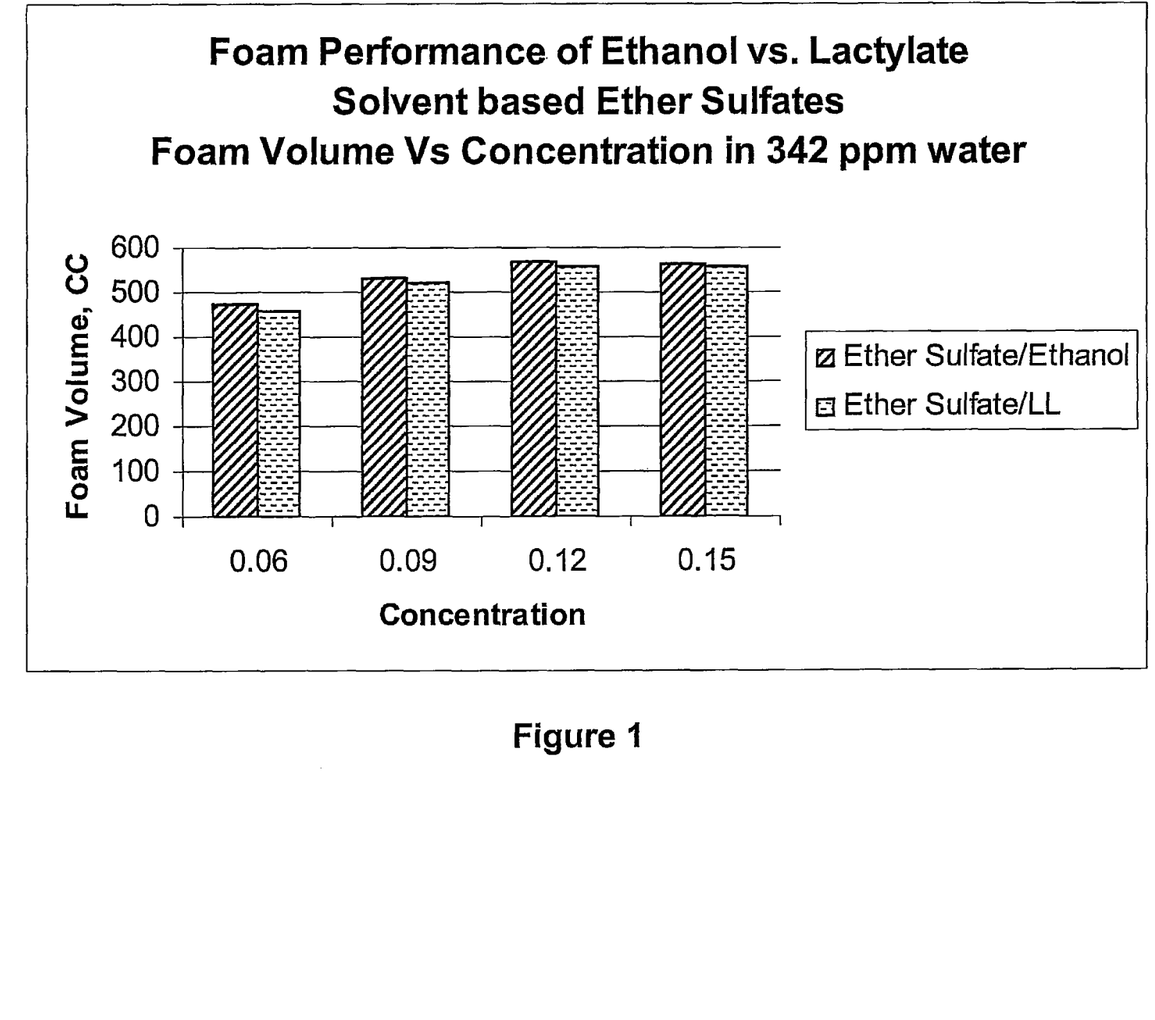
FIG. 1 is a bar graph illustrating the foam volume performance of an ether sulfate foaming agent in a conventional ethanol solvent and an alkyl lactyllactate solvent of the present technology.
Figure 2:
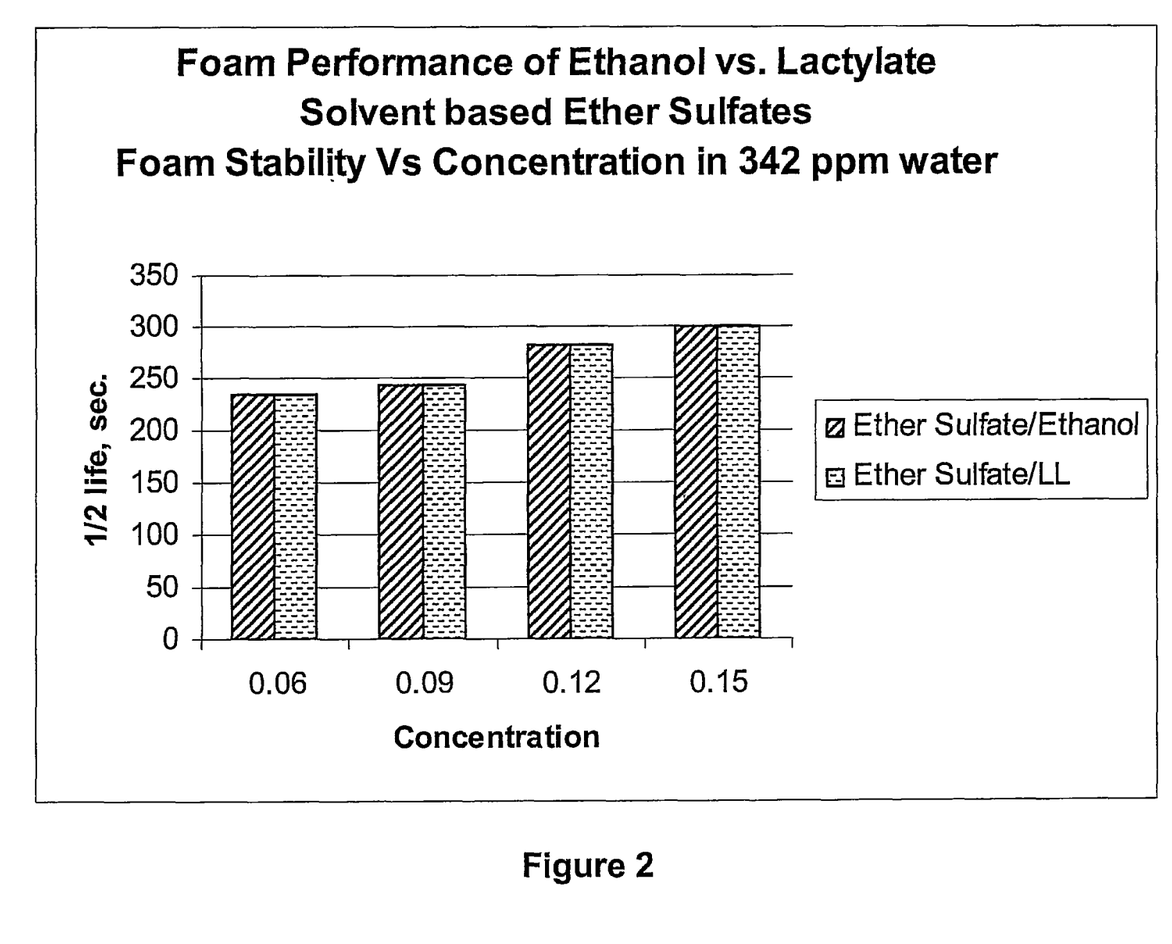
FIG. 2 is a bar graph illustrating the foam stability performance of an ether sulfate foaming agent in a conventional ethanol solvent and an alkyl lactyllactate solvent of the present technology.

From the FIG. 1 and FIG. 2 graphs, it can be seen that the foam volume and the foam stability of the two samples are about the same, indicating that the foam performance of the ether sulfate is not degraded by the use of the lactyllactate ester solvent. The foam test results further demonstrate that the lactyllactate ester is a suitable solvent for ether sulfate foaming applications and provides the further advantages of low VOC and high flashpoint compared to conventional solvents such as ethanol.

EXAMPLE 6

Preparation of a Lactyllactate Ester Using Meso-Lactide and Butyl Carbitol™

In a 500 g resin kettle with an overhead mixer, condenser, and thermometer attachment, 266.0 grams of Butyl Carbitol™ (diethylene glycol monobutyl ether), available from Dow Chemical Co., was mixed with 235.24 grams of Meso-lactide (85% Meso-lactide/15% L-lactide). The mixture was heated to 70° C., and 0.24 grams of sulfuric acid were added. The temperature was set to 120° C. and the reaction was allowed to run for three hours. The heat was turned off and the product allowed to cool. The product was a light yellow homogeneous liquid. A pour point analysis of the resulting product was conducted in accordance with ASTM D97-02. The lactyllactate ester had a pour point of −44.4° C.

EXAMPLE 7

Evaluation of Lactyllactate Esters having Different Chiralities

Three lactyllactate ester samples were prepared using Butyl Carbitol™ and racemic lactide, L-lactide and meso-lactide (85% Meso-lactide/15% L-lactide), respectively. The amounts and procedure for each sample are described in Table 4 below.

TABLE 4

| Name | Mass (grams) | Mole | Equiv |
|---|---|---|---|
| Sample 1 | | | |
| Lactide SS/RR (racemic) | 18.87 | 0.13094 | 1.000 |
| Butyl Carbitol | 21.25 | 0.13097 | 1.000 |
| Add butylcarbitol (liquid) to lactide (solid) in 4 ox jar. Add 64.3 mg H2SO4, cap, and shake. Place in 69° oven for 2 hr; most solid gone. Place in 50° C. oven overnight, no solid remaining. Remove from oven. | | | |
| Sample 2 | | | |
| Lactide SS | 24.10 | 0.16723 | 1.000 |
| Butyl Carbitol | 27.16 | 0.16744 | 1.001 |
| Add butylcarbitol (liquid) to lactide (solid) in 4 oz jar. Add 95 mg H2SO4, cap, and shake. Place in 69° C. oven for 2 hr; solid present. Place in 50° C. oven overnight, still solid. Place in 69° C. oven. | | | |
| Sample 3 | | | |
| Meso-lactide | 48.27 | 0.33487 | 1.000 |
| Butyl Carbitol | 54.36 | 0.33506 | 1.001 |
| Add butylcarbitol (liquid) to lactide in 4 oz jar (miscible). Add 70 mg H2SO4, cap, and shake. Place in 69° C. oven for 2 hr; slightly yellow. Place in 50° C. oven overnight, slightly yellow. Remove from oven. | | | |

Each of the samples 1, 2 and 3 were evaluated as a solvent for Steol-CS370, a sodium laureth sulfate containing 3 moles of ethoxylate, and compared against Steol CS370 (70% actives) combined with the conventional solvents ethanol (comparative 1) and hexylene glycol (comparative 2), and with Steol CS370 with water alone and no solvent (comparative 3). The sample amounts and procedures are shown in Table 5.

TABLE 5

|  | Grams | % Active |
|---|---|---|
| Steol-CS370 |  | 70 |
| Solvent |  | 100 |
| Added H$_2$O | DI | 100 |
| Steol-CS370 | 34 | 38 |
| Solvent | 18 | 29 |
| Added H$_2$O | 11 | 34 |
| For each sample add the solvent to the Steol-CS370 in a 4 oz jar; Shake to disperse. Add the added water and shake further to give a homogeneous fluid. | | |
| Sample 1 | | |
| Steol-CS370 | 34.2547 | 37.73 |
| Racemic lactide | 18.21 | 28.65 |
| Added H$_2$O | 11.0943 | 33.62 |
| Sample 2 | | |
| Steol-CS370 | 32.6703 | 37.42 |
| L-lactide | 17.3444 | 28.38 |
| Added H$_2$O | 11.0944 | 34.19 |
| Sample 3 | | |
| Steol-CS370 | 33.4601 | 38.20 |
| Meso-lactide | 17.73 | 28.92 |
| Added H$_2$O | 10.1165 | 32.87 |
| Comparative 1 | | |
| Steol-CS370 | 35.5111 | 37.75 |
| Ethanol | 18.8042 | 28.56 |
| Added H$_2$O | 11.5341 | 33.69 |
| Comparative 2 | | |
| Steol-CS370 | 33.7434 | 37.74 |
| Hexylene Glycol | 17.8451 | 28.52 |
| Added H$_2$O | 10.9923 | 33.74 |
| Comparative 3 | | |
| Steol-CS370 | 30.809 | 37.76 |
| Water | 16.326 | 28.58 |
| Added H$_2$O | 9.9853 | 33.66 |
| Formed gel, did not recover | | |

Each of the samples 1, 2 and 3, and comparative samples 1 and 2 shown in Table 5 above were evaluated for pour point in accordance with ASTM D97-02. The pour point results are shown in Table 6 below.

TABLE 6

|  | Pour Point | |
|---|---|---|
| Sample ID | Degrees C. | Degrees F. |
| Sample 1 | −15.2 | 4.6 |
| Sample 2 | −16.6 | 2.1 |
| Sample 3 | −13.4 | 7.9 |
| Comparative 1 | −14.7 | 5.6 |
| Comparative 2 | −13.7 | 7.4 |

From the pour point data shown in Table 6, it can be seen that both sample 1 (racemic lactyllactate) and sample 2 (L-lactyllactate) had better pour points than either of the comparative samples made with conventional solvents, with sample 2 providing the best results. Although the pour point of sample 3 was not improved over that of the conventional solvents, sample 3, as well as samples 1 and 2, have low VOC and higher flashpoints, which are important advantages over conventional solvents. These results demonstrate that at least some of the lactyllactate esters of the present technology provide improved results in terms of lower pour points compared to conventional solvents. Moreover, these lactyllactate esters have low VOC and higher flashpoints than conventional solvents, making the lactyllactate esters suitable for use in applications requiring cold tolerance performance without inclusion of additional volatile components.

EXAMPLE 8

Evaluation of Butyl Carbitol™ Based Lactyllactate with Different Active Levels of Ether Sulfates Diethylene glycol monobutyl ether lactyllactate prepared from Butyl Carbitol™ and lactide was used as a solvent for different ether sulfates at 50%, 60% and 65% active. The ether sulfates used were an ether sulfate and a C8-10+1EO ether sulfate ammonium salt. In addition to varying the actives level of the ether sulfate, the ratio of lactyllactate to water in the solvent system was also varied. The results of the solvent evaluation are set forth in Table 7 below.

TABLE 7

| Surfactant (active) | C4-2LL/Water | @25 C. | @50 C. | After cooling to 25 C. | @3 C. | <−20 C. (freezer overnight) |
|---|---|---|---|---|---|---|
| Ether sulfate (50%) | 50/50 | Clear liquid | Clear liquid | Clear liquid | Clear liquid | Clear liquid |
| Ether sulfate (60%) | 50/50 | Clear liquid | Clear liquid | Clear liquid | Clear liquid | Clear liquid |
| Ether sulfate (65%) | 50/50 | Clear liquid | Clear liquid | Clear liquid | Clear liquid | Clear liquid |
| Ether sulfate (65%) | 60/40 | Hazy liquid | Wispy & clear liquid | Clear liquid | Clear liquid | Clear liquid |
| C8-10 + 1EO ether sulfate ammonium salt (50%) | 60/40 | Clear liquid | Clear liquid | Clear liquid | Clear liquid | Clear liquid |
| C8-10 + 1EO ether sulfate ammonium salt (50%) | 70/30 | Clear liquid | Clear liquid | Clear liquid | Clear liquid | Clear liquid |
| C8-10 + 1EO ether sulfate ammonium salt (50%) | 80/20 | Clear liquid | Clear liquid | Clear liquid | Clear liquid | Clear liquid |

The results demonstrate that the lactyllactate ester is a suitable non-VOC solvent for ether sulfates having high actives concentrations. The results further demonstrate that the lactyllactates ester/water ratio in the solvent system can be varied while still obtaining a clear liquid product.

Pour points for the sample products prepared above were measured in accordance with ASTM D97-02. The pour point results are set forth below in Table 8.

TABLE 8

| Sample ID | Actives | Pour Point Degrees C. | Pour Point Degrees F. |
|---|---|---|---|
| C8-10 + 1EO ether sulfate ammonium salt with 60% C4 LL | 50 | −45.6 | −50.0 |
| C8-10 + 1EO ether sulfate ammonium salt with 70% C4 LL | 50 | −41.6 | −42.8 |
| C8-10 + 1EO ether sulfate ammonium salt with 80% C4 LL | 50 | −28.9 | −20.0 |
| Ether sulfate with 50% C4 LL | 50 | −28.8 | −19.8 |
| Ether sulfate with 50% C4 LL | 65 | −55.7 | −68.2 |
| Ether sulfate with 60% C4 LL | 50 | −37.3 | −35.2 |
| Ether sulfate with 60% C4 LL | 65 | −55.9 | −68.6 |

From the pour point results, it can be seen that the diethylene glycol monobutyl ether lactyllactate can achieve pour points lower than −50° C. when combined with the ether sulfates. This result is surprising and unexpected because the lactyllactate ester alone and the ether sulfate alone both have higher pour points than −50° C. One would expect that the pour point from the combination of lactyllactate ester and ether sulfate to be somewhere in the range between the separate pour points of the individual components. Thus, it is completely unexpected that the pour point of the combination would be lower than either of the pour points of the components themselves and that the pour point could be lower than −50° C.

Further, it can be seen from the pour point results that the pour point of the final product can be adjusted by varying the % actives of the ether sulfate or the lactyllactate ester/water ratio or both.

EXAMPLE 9

Use of Lauryl Lactyllactate as a Coalescing Agent for Polymer Films 100 grams of 3106-55 styrene-acrylic latex (47.5% solids) was pH adjusted from 7.2 to 8.2 using 3.5 N ammonium hydroxide. 0.9 grams of Acrysol SCT-275 thickener was blended in and mixed for 10 minutes. The final viscosity was about 350 cp. The thickened latex was divided up into 30 gram portions. 1.5 grams of Texanol Ester Alcohol (2,2,4-Trimethyl-1,3-pentanediol Monoisobutyrate) coalescing solvent was added to one portion, 1.5 grams STEPAN MILD® L3 (lauryl lactyllactate) added to a second portion. 75 um wet films of the two blended samples along with latex without added coalescing agent were then applied to a pre-conditioned Rhopoint MFFT-Bar. 90 minimum film formation temperature instrument. The instrument was set to range #1 (−5 to 13° C.). After about an hour, the latexes containing coalescing agents had MFFT values below 5° C. The latex without coalescing solvent did not form a coalesced film (MFFT >13° C.). In a separate experiment, it was determined that the MFFT for the latex without coalescing agent was 22° C.

EXAMPLE 10

Preparation of Liquid Graffiti Removers

Liquid graffiti removers having the formulations shown in Table 9 below are prepared by combining the ingredients in the order listed and mixing well until a homogeneous mixture is obtained.

TABLE 9

| Graffiti Remover | | | |
|---|---|---|---|
| Ingredients | % Active | % Active | % Active |
| L3 (Lauryl lactyllactate) | 25 | 30 | 45 |
| Soya methyl ester | 12.5 | 10 | — |
| Ethyl lactate | 12.5 | 10 | — |
| Alcohol ethoxylate | 10 | 10 | 10 |
| d-limonene | 40 | 40 | 45 |

EXAMPLE 11

Preparation of Varnish Removers

Varnish removers having the formulation shown in Table 10 below are prepared by combining the ingredients in the order listed and mixing well until a homogeneous mixture is obtained.

TABLE 10

| Varnish Remover | | | |
|---|---|---|---|
| Ingredients | % Active | % Active | % Active |
| L3 (Lauryl lactyllactate) | 20 | — | — |
| Ethyl lactyllactate | — | 30 | 50 |
| Ethyl lactate | 15 | 10 | 20 |
| Soya methyl ester | 15 | 10 | — |
| d-limonene | 46 | 45 | 26 |
| Ethanol | 4 | 5 | 4 |

EXAMPLE 12

Preparation of Carbon Mark Removers

Liquid carbon mark removers having the formulations shown in Table 11 below are prepared by combining the ingredients in the order listed and mixing well until a homogeneous mixture is obtained.

TABLE 11

| Carbon Mark Remover | | |
|---|---|---|
| Ingredients | % Active | % Active |
| L3 (Lauryl lactyllactate) | 30 | — |
| Ethyl lactyllactate | — | 40 |
| Soya methyl ester | 30 | 20 |
| Ethyl lactate | 20 | 20 |
| d-limonene | 9 | 9 |
| Alcohol ethoxylate | 10 | 10 |
| Alkanolamide | 1 | 1 |

EXAMPLE 13

Preparation of a Carpet Traffic Spotter

A carpet traffic spotter with a formulation shown in Table 12 below is prepared by combining the ingredients in the order listed and mixing well until a homogeneous mixture is obtained.

TABLE 12

Carpet Traffic Spotter

| Ingredients | % Active |
|---|---|
| methyllactyllactate | 4 |
| Glycol ether | 2 |
| Alcohol sulfate | 1.5 |
| Amine oxide | 0.2 |
| Water | balance |

EXAMPLE 14

Preparation of a Waterless Hand Cleaner

A waterless hand cleaner with a formulation show in Table 13 below is prepared by the following procedure:

Add all ingredients except water together and mix until clear. Heat to 70° C.-80° C. Slowly add deionized water with mixing. Once the water is dispersed begin cooling to room temperature. A thick gel forms.

TABLE 13

Waterless Hand Cleaner

| Ingredients | % Active |
|---|---|
| Alcohol ethoxylate | 11 |
| Alkanolamide | 4 |
| L3 (lauryl lactyllactate) | 17 |
| Fatty acid | 1.6 |
| Triethanolamine, 85% | 0.4 |
| d-limonene | 17 |
| Preservative | 0.1 |
| Deionized water | 49.9 |

EXAMPLE 15

Preparation of Thick Gel Waterless Cleaners

Thick gel waterless cleaners having the formulation shown below in Table 14 are prepared by the following procedure:

Combine all the ingredients except thickener. While mixing, heat to 155° F.-165° F. Charge the thickener at 155° F.-165° F. and mix. Reduce the temperature and continue to mix until cooled to room temperature.

TABLE 14

Thick Gel Waterless Cleaner

| Ingredients | % Active | % Active |
|---|---|---|
| L3 (Lauryl lactyllactate) | 25 | 37.5 |
| Soya methyl ester | 25 | — |
| Ethyl lactate | 25 | 37.5 |
| Alcohol ethoxylate | 15 | 15 |
| Thickener | 10 | 10 |

The lauryl lactyllactate used as a component in any of the above formulations in Examples 10 to 15 can be derived from L-lactide, meso-lactide, or a mixture of L-lactide and meso-lactide.

EXAMPLE 16

Evaluation of Alkyl Lactyllactates in Degreaser Compositions

A degreaser composition is prepared with the comparative formulation shown in Table 15 below by combining the ingredients and mixing until a homogeneous mixture is obtained. Four experimental sample formulations are also prepared by a similar method. For experimental sample 1, lauryl lactyllactate is substituted for the soya methyl ester and for experimental sample 2, lauryl lactyllactate is substituted for both the ethyl lactate and the soya methyl ester components in the comparative formulation. For experimental sample 3, ethyl lactyllactate is substituted for the soya methyl ester and for experimental sample 4, ethyl lactyllactate is substituted for both the ethyl lactate and soya methyl ester components. The experimental sample formulations are shown below in Table 15. Another comparative composition containing dimethyl sulfoxide, a known grease cutter, is also shown in Table 15 below.

TABLE 15

| Ingredients | Comparative 1 % Active | Sample 1 % Active | Sample 2 % Active | Sample 3 % Active | Sample 4 % Active | Sample 5 % Active |
|---|---|---|---|---|---|---|
| Ethyl lactate | 25 | 25 | — | 25 | — | — |
| Soya methyl ester | 25 | — | — | — | — | — |
| d-limonene | 50 | 50 | 50 | 50 | 50 | 50 |
| Lauryl lactyllactate | — | 25 | 50 | — | — | — |
| Ethyl lactyllactate | — | — | — | 25 | 50 | — |
| Dimethyl Sulfoxide | — | — | — | — | — | 50 |
| Results | Middle | Best | Best | Best | Best | Worst |

Each of the experimental samples, the Table 15 comparative composition and the Sample 5 comparative composition are evaluated for degreasing ability in accordance with the following grease removal test:

Grease Removal Test

Cover the surface of a clear-coated stainless steel plate with a layer of grease. Then place two droplets of the sample formulation on the plate and allow them to stand for 60 seconds. Observe how well the droplets spread and wet the surface.

Carry the plate to a sink in a horizontal position as it was on the lab bench and then, when at the sink, tip the plate vertically allowing the droplets to run down the plate.

Rinse water over the droplets for 15 seconds and then allow the plate to dry in an upright position.

Best grease removal indicates that the surface of the plate where the droplets were placed may be seen free or substantially free of grease.

Middle grease removal indicates that much of the grease was removed, but some remains where the droplets were placed.

Worst grease removal indicates that little or no grease was removed from the plate.

The test compositions in which the lauryl lactyllactate and the ethyl lactyllactate are substituted for the soya methyl ester, and the test compositions in which the lauryl lactyllactate and ethyl lactyllactate are substituted for both the soya methyl ester and ethyl lactate, have results in the "best grease removal" category. The test composition comprising ethyl lactyllactate, ethyl lactate and d-limonene, had slightly less grease removal than the other three test compositions. By comparison, the Table 15 comparative composition has grease removal results in the "middle" category, and the dimethyl sulfoxide grease remover has results in the "worst" category. The test results demonstrate that at least some of the alkyl lactyllactates of the present technology can be used as solvents in degreaser compositions to give degreasing performance that is superior to known grease removal compositions.

EXAMPLE 17

Preparation of Heavy Duty Cleaner/Degreasers

Heavy duty cleaner/degreaser compositions having the formulations shown in Table 16 below are prepared by the following procedure:

Add surfactants and glycol ether to d-limonene and mix until clear. Add water slowly, while under high agitation. Mix until clear.

TABLE 16

Heavy Duty Cleaner/Degreaser

| Ingredients | % Active | % Active |
| --- | --- | --- |
| L3 (lauryl lactyllactate) | 25 | — |
| Ethyl lactyllactate | — | 30 |
| d-limonene | 25 | 20 |
| Alkanolamide | 9.5 | 9.5 |
| Alcohol ethoxylate | 5 | 5 |
| Amine oxide | 0.5 | 0.5 |
| Glycol ether | 10 | 10 |
| Water | 25 | 25 |

The compositions can be used as is or diluted with water to remove oily soils.

The present technology is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the present technology as set forth in the appended claims.

The invention claimed is:

1. A solvent composition comprising:
    at least one alkyl lactyllactate reaction product comprising alkyl lactyllactate of the following general structure:

wherein, R is an alkyl group or alkoxylated alkyl group derived from a hydroxyl containing compound and contains about six to about eighteen carbon atoms; and
    wherein the alkyl lactyllactate reaction product is derived from an L-lactide or L lactic acid source;
    at least one alkyl ether sulfate comprising about six to about 10 carbon atoms or a salt thereof, wherein the alkyl ether sulfate or a salt thereof comprises more than 40% by weight of the composition; and
    optionally at least one additive,
    the composition has a pour point that is lower than the pour point of a composition not containing or incorporating the alkyl lactyllactate reaction product.

2. The composition of claim 1, wherein R is an alkoxylated alkyl group.

3. The composition of claim 2, wherein the alkoxylated lactyllactate is diethyleneglycol monobutyl ether lactyllactate.

4. The composition of claim 1, wherein the composition is substantially free of volatile organic compounds.

5. The composition of claim 1, wherein the composition has a pour point that is less than about −50° Celsius.

6. The composition of claim 1 wherein the composition has a pour point that is less than about −25° C.

7. The composition of claim 1, wherein the additive is a member selected from the group consisting of soya methyl ester, ethyl lactate, d-limonene, alkanolamides, short chain alcohols, derivatives thereof, and combinations thereof.

8. A solvent composition comprising:
    at least one alkyl lactyllactate reaction product comprising an alkyl lactyllactate of the following general structure:

wherein, R is an alkyl group or alkoxylated alkyl group derived from a hydroxy containing compound and contains about six to about eighteen carbon atoms;
    wherein the alkyl lactyllactate is derived from a meso-, racemic, or mixture thereof lactide or lactic acid source;
    at least one alkyl ether sulfate comprising about six to about 10 carbon atoms or a salt thereof, wherein the alkyl ether sulfate or a salt thereof comprises more than 40% by weight of the composition; and
    optionally at least one additive,
    the composition has a pour point that is lower than the pour point of a composition not containing or incorporating the alkyl lactyllactate reaction product.

9. The composition of claim 8, wherein R is an alkoxylated alkyl group.

10. The composition of claim 9, wherein the alkoxylated lactyllactate is diethyleneglycol monobutyl ether lactyl lactate.

11. The composition of claim 8, wherein the pour point of the composition is about −5° Celsius or less.

12. The composition of claim 8, wherein the composition has a pour point that is less than about −50° Celsius.

13. The composition of claim 8, wherein the composition has a pour point that is less than about −25° C.

14. The composition of claim 8, wherein the additive is a member selected from the group consisting of soya methyl ester, ethyl lactate, d-limonene, alkanolamines, short chain alcohols, derivatives thereof, and combinations thereof.

* * * * *